United States Patent [19]

Maxwell

[11] Patent Number: 4,928,694
[45] Date of Patent: May 29, 1990

[54] INTRAVASCULAR BLOOD PARAMETER MEASUREMENT SYSTEM

[75] Inventor: Thomas P. Maxwell, Santa Ana, Calif.

[73] Assignee: Minnesota Mining and Manufacturing Company, St. Paul, Minn.

[21] Appl. No.: 328,041

[22] Filed: Mar. 23, 1989

Related U.S. Application Data

[62] Division of Ser. No. 8,937, Jan. 30, 1987, Pat. No. 4,830,013.

[51] Int. Cl.$^5$ .............................................. A61B 5/00
[52] U.S. Cl. ..................................... 128/637; 128/634
[58] Field of Search ............... 128/637, 632, 635, 634, 128/692, 673

[56] References Cited

U.S. PATENT DOCUMENTS

| | | | |
|---|---|---|---|
| 2,629,399 | 2/1953 | Kulick | 604/118 |
| 3,498,286 | 3/1970 | Polanyi et al. | 128/673 |
| 3,612,866 | 10/1971 | Stevens | 250/483.1 |
| 3,616,409 | 10/1971 | Tosteson | 204/195 |
| 3,674,013 | 4/1972 | Palanyi | 356/241 |
| 3,807,390 | 4/1974 | Ostrowski et al. | 356/41 |
| 3,866,599 | 2/1975 | Johnson | 128/348 |
| 4,050,450 | 9/1977 | Polanyi et al. | 356/41 |
| 4,073,297 | 2/1978 | Kopp | 604/44 |
| 4,201,222 | 5/1980 | Haase | 128/673 |
| 4,210,029 | 7/1980 | Porter | 128/673 |
| 4,295,470 | 10/1981 | Shaw et al. | 128/634 |
| 4,311,137 | 1/1982 | Gerard | 604/28 |
| 4,322,164 | 3/1982 | Shaw | 356/243 |
| 4,398,542 | 8/1983 | Cunningham | 128/675 |
| 4,407,290 | 10/1983 | Wilbur | 128/633 |
| 4,471,765 | 9/1984 | Strauss et al. | 128/655 |
| 4,476,877 | 10/1984 | Barker | 128/236 |
| 4,502,488 | 3/1985 | Degironimo et al. | 128/692 |
| 4,508,123 | 4/1985 | Wyatt et al. | 128/692 |
| 4,557,900 | 12/1985 | Heitzmann | 422/55 |
| 4,573,968 | 3/1984 | Parker | 604/67 |
| 4,585,007 | 3/1986 | Uchigaki | 128/632 |
| 4,601,706 | 7/1986 | Aillon | 128/673 |
| 4,608,996 | 11/1988 | Brown et al. | 128/760 |
| 4,640,820 | 2/1987 | Cooper | 422/68 |
| 4,651,741 | 3/1987 | Passafaro | 128/633 |
| 4,684,245 | 8/1987 | Goldring | 356/41 |
| 4,718,423 | 1/1988 | Willis et al. | 128/634 |
| 4,736,748 | 3/1988 | Nakamura et al. | 128/632 |
| 4,774,955 | 10/1988 | Jones | 128/632 |
| 4,785,814 | 11/1988 | Kane | 128/634 |
| 4,810,655 | 3/1989 | Khalil | 436/138 |

Primary Examiner—Francis Jaworski
Assistant Examiner—George Manuel
Attorney, Agent, or Firm—Donald M. Sell; Walter N. Kirn; Dale E. Hulse

[57] ABSTRACT

A parameter of blood is sensed in vivo with a system which includes a catheter and a probe. The catheter has a lumen extending therethrough, a proximal end, a distal end and a distal opening at the distal end. The probe includes one or more sensors at its distal end. A saline solution is introduced into the lumen so that there is an interface adjacent the distal opening of the catheter between the blood and saline solution. The probe is received within the catheter and affixed thereto. The interface is moved back and forth in the lumen to expose the sensors to blood so that they can sense the blood parameters of interest.

21 Claims, 3 Drawing Sheets

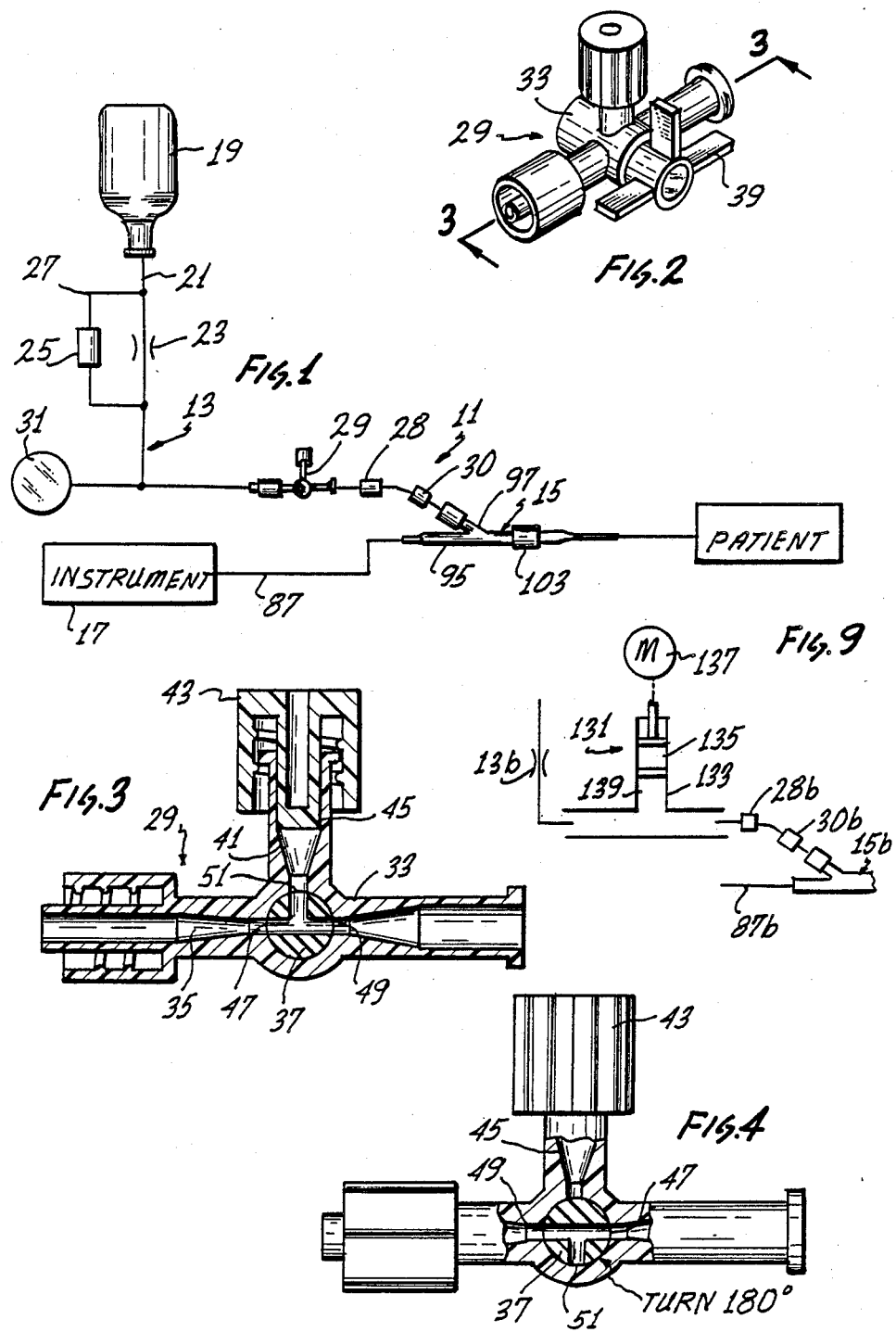

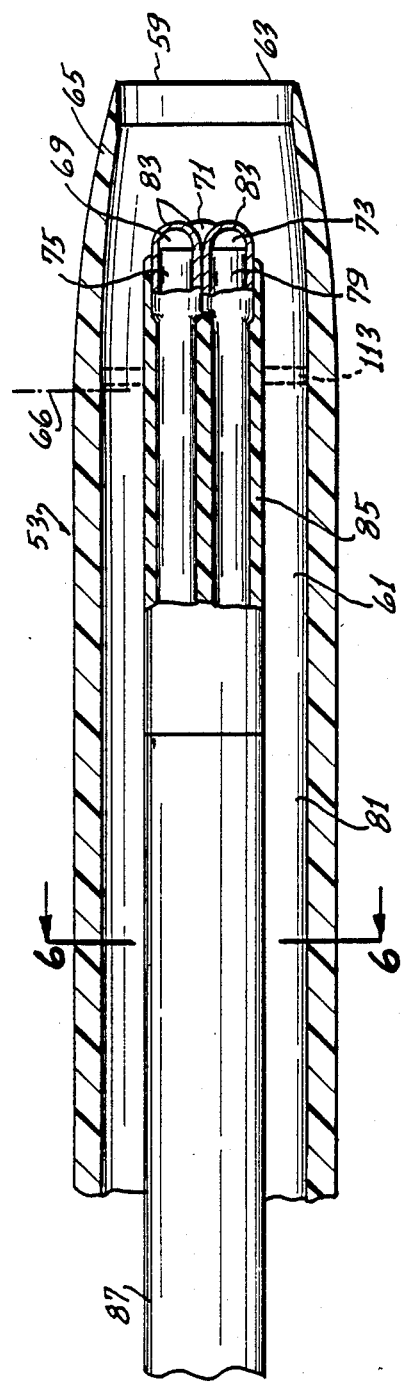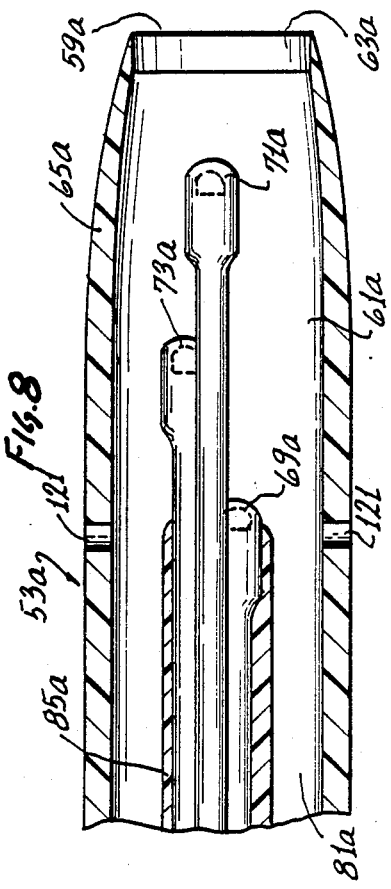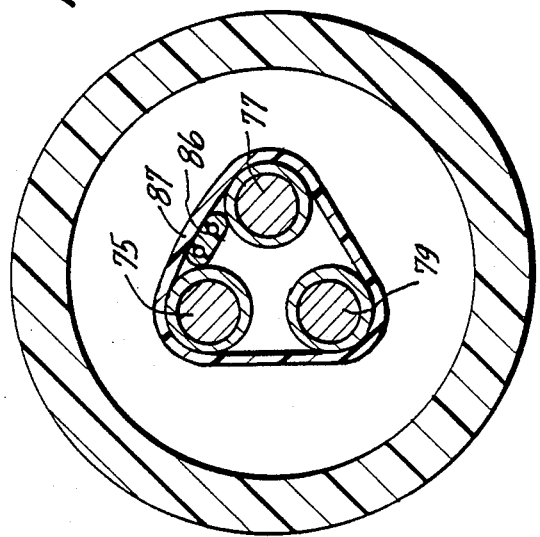

INTRAVASCULAR BLOOD PARAMETER MEASUREMENT SYSTEM

This application is a continuation of application Ser. No. 008,937, filed Jan. 30, 1987 now U.S. Pat. No. 4,830,013.

BACKGROUND OF THE INVENTION

It is often necessary or desirable to measure various parameters of blood, such as temperature and blood constituents, such as blood gases, pH, other electrolytes and glucose. This can be accomplished in real time using fluorescent sensors. For example, this can be accomplished in an extracorporeal blood loop as shown in Cooper Application Ser. No. 546,493 filed on Oct. 28, 1983, and in vivo as disclosed in Lubbers et al Reissue Pat. No. 31,879. For in vivo sensing, a probe or catheter carrying an appropriate sensor is inserted into a blood vessel of the patient.

One of the most important gases that needs to be sensed is oxygen. One problem with in vivo oxygen sensing is that the readings obtained for the concentrations of oxygen tend to vary over an unacceptably wide range when compared with the results obtained using conventional laboratory techniques for measuring the concentration of oxygen. It has been found that this deviation is in many cases unacceptably large so that the reliability of the in vivo measuring system is called into question.

SUMMARY OF THE INVENTION

At least one feature of the invention is based, in part, upon the recognition and discovery of the reasons why unacceptable results were often obtained in the in vivo system. Specifically, I have discovered that the oxygen readings are subject to a "wall effect" in that lower concentration readings are obtained when the oxygen sensor is against the wall of the vessel in which it is placed. Although this invention is not to be limited by any particular theory, one possible reason for the "wall effect" is that the concentration of oxygen in the blood may be different at the vessel wall than at a more central location within the vessel, or the low level of oxygen in the adjacent tissue may cause the oxygen concentration in the vessel wall to be low compared to the concentration in the blood. In addition, there is a "clot effect" which reduces the oxygen readings when a clot forms over the oxygen sensor. The clot may also effect other readings, such as by increasing the reading for the concentration of $CO_2$ and reducing the reading for the pH value. The "wall effect" and the "clot effect" are independent, but they can exist at the same time, as well as separately.

Having recognized these two problems, i.e., the "wall effect" and the "clot effect", this invention solves these problems by keeping the sensors, and in particular, the oxygen sensor from contacting the wall of the vessel in which it is placed. This reduces or eliminates the "wall effect" on the oxygen reading. In addition, it reduces the tendency of the blood to form a clot around the sensors. Accordingly, by keeping the sensors out of contact with the wall of the vessel, these two problems are minimized, and acceptable readings are obtainable.

Techniques exist for keeping various in vivo sensors out of contact with the vessel wall; however, none of these are directed toward solving the "wall effect" or the "clot effect." For example, Schuette U.S. Pat. No. 3,529,591, uses a shield around electrodes to confine the electric field seen by the electrodes in an attempt to minimize interference created through contacting the wall of the vessel. U.S. Pat. No. 4,478,222 employs a sensor within a catheter having a radial opening and also is not concerned with the "wall effect" or the "clot effect."

Although the means for keeping the sensor from contacting the wall can take different forms, it preferably includes a tubular body having an opening, and the sensor is positioned within the tubular body. The tubular body can advantageously take the form of a catheter. To facilitate blood flow into the catheter and to minimize the likelihood that the opening will be shut off by contact with the vessel wall, the opening is preferably a distal opening at the distal end of the catheter. One or more radial apertures may be provided in addition to the distal opening, if desired.

The sensor can be mounted within the catheter in any desired way. A preferred system includes a probe-catheter assembly which comprises a probe including at least one sensor for sensing a parameter of blood and providing a signal in response thereto and elongated transmission means for transmitting the signal from the sensor proximally. The sensor is carried by a distal portion of the transmission means. The assembly also includes the catheter which has a lumen extending therethrough, a proximal end, a distal end and a distal opening at the distal end.

When utilizing a probe-catheter assembly of this type, the catheter can be used to keep the sensor from contacting the wall of the vessel. This can be advantageously accomplished by attaching the probe to the catheter such that the sensor of the probe is within the lumen of the catheter and adjacent the distal opening of the catheter. With this construction, the sensor is shielded from the wall of the vessel by the catheter but is not located so far back within the catheter that it cannot perform its sensing function.

It is quite surprising that a sensor located within a catheter lumen could adequately sense the parameter of interest in blood. One reason for this is that it is necessary to introduce an anti-clotting solution, such as a heparinized saline solution, into the lumen from a solution-introducing system. The solution may be resident in the lumen, i.e., have no net flow into the vessel, but preferably it flows at a very low rate, such as 3 to 8 milliliters per hour, through the lumen and out through the distal opening of the catheter into the blood stream in the vessel. It is surprising that a sensor positioned in the lumen where there is an anti-clotting solution, particularly in the path of the distally flowing anti-clotting solution, would be able to adequately sense the parameters of interest in blood.

However, this invention recognizes that there is an interface between the blood and the anti-clotting solution. Theoretically, the interface could be a plane that simply divides the blood from the anti-clotting solution. However, in reality, the interface is a zone which has some axial length and which contains a mixture of the blood and the anti-clotting solution. Thus, the interface divides a zone of substantially all blood from a zone containing substantially all anti-clotting solution.

Because the anti-clotting solution may be supplied to the catheter such that there is a net flow of solution through the distal opening to the vessel, it would be expected that the interface would be entirely outside of, or at the distal end of, the catheter. However, by moving the interface back and forth in the lumen, the sensor can be exposed to blood for at least a portion of time that the interface is moving. This exposure must be sufficient to enable the sensor to provide an accurate signal related to the blood parameter of interest.

The movement of the interface back and forth in the lumen may move the interface over the sensor. However, the sensors, and in particular the oxygen sensor, can tolerate some exposure to the mixture of anti-clotting solution and blood in the interface without providing erroneous readings. For example, it has been found that a mixture consisting of 50 percent blood by volume and 50 percent anti-clotting solution by volume yields approximately the same oxygen concentration as the oxygen concentration in a medium consisting essentially of blood.

Movement of the interface to bathe the sensor within the lumen in blood can be brought about in different ways. For example, the interface may be moved by varying the delivery pressure and/or volume of the anti-clotting solution or providing the introducing system with a volume oscillator and allowing the volume oscillator to move the interface. The volume oscillator may, for example, take the form of a syringe which, in effect, expands and contracts the volume of the introducing system to move the blood back and forth in the lumen without creating a net or average flow in either direction.

Another technique for moving the blood back and forth in the lumen, which also enables expansion and contraction of the volume of the introducing system, includes providing the introducing system with some compliance and allowing pressures generated by the patient's heartbeats to move the interface. Consequently, blood is forced to enter the distal opening of the catheter as the blood pressure rises with each beat of the heart. Thus, the interface is caused to flow back and forth in the lumen with the pulsating blood pressure. As a result, the sensor within the lumen is bathed by the back and forth or tidal movement of the blood and can adequately sense and measure the blood parameters of interest.

The compliance of the introducing system may be the natural compliance of the tubing and components of the system and/or a compliant element may be added to the system to provide the desired degree of elasticity. The compliant element can be of virtually any construction and may be, or include for example, a compressible fluid, such as air, a membrane, a bellows, etc. The compliance of the introducing system may be varied to obtain the results desired. For example, if the compliance of the introducing system is to be used to obtain, or to assist in obtaining, the tidal action, the introducing system and the catheter may have a combined total compliance sufficient to provide a volume exchange of at least 10 microliters with a system comprised of a 20-gauge catheter and 0.022 inch diameter probe.

It may be necessary or desirable to take the patient's blood pressure through the lumen of the catheter while the blood parameters are being sensed. The added compliance of the introducing system may be sufficient to undesirably alter the blood pressure readings taken through the lumen of the catheter. Accordingly, the present invention provides, as an option, for selectively nullifying the ability of the compliant element to allow expansion and contraction of the volume of the introducing system. For example, the nullifying means may control expansion or adjustably limit movement of a membrane or bellows or it may selectively switch the compliant element into, and out of, communication with the lumen of the catheter. In this latter event, the compliant element would normally be in communication with the lumen to provide, or assist in providing, the desirable tidal action for sensing of the blood parameters of interest. However, just prior to taking a blood pressure reading, the action of the compliant element can be switched out of the introducing system so that it cannot affect the blood pressure reading taken through the lumen of the catheter. The switching means may take any form that will accomplish this function and may be, for example, a valve.

To assure that the sensor will not contact the vessel wall, the sensor preferably does not protrude beyond the distal opening of the catheter. It is desirable to have the sensor located proximal to the distal opening of the catheter to provide added insurance against contact with the wall of the vessel. Similarly, the sensor should not be located so far proximal to the distal opening that it cannot adequately sense the parameter of interest. Thus, the sensor should not be so far proximal that it cannot be adequately bathed by the blood. This distance will vary depending on how far the blood is drawn into the lumen. Although the specific distances can vary, for example, placing the sensor between 0.005 inch proximal to the distal opening and 0.125 inch proximal to the distal opening has been found satisfactory. The 0.005 inch dimension is usually sufficient to provide for tolerance variations that, if added together, might cause the sensor to protrude from the lumen.

The probe may carry one or more sensors depending upon the number of parameters of interest. These sensors can be of any type, such as electro-chemical, that is suitable for sensing the parameter of interest; however, optical sensors are preferred, and fluorescent sensors are considered optimum. Although multiple sensors could be provided to sense the same blood parameter, preferably, each sensor senses a different blood parameter. In a preferred construction, the transmission means includes an optical fiber for each of the sensors, with the sensor being located on the distal end of the associated optical fiber. The sensors provide signals related to the associated blood parameters of interest, and such signals may be used or processed continuously, intermittently or on demand to provide readings indicative of the blood parameters of interest.

A conventional catheter usable with this invention has a standard lead-in taper, i.e., the cross-sectional area of the lumen reduces toward the distal opening in a zone closely adjacent the distal opening. The presence of the probe in this tapered zone tends to reduce the remaining open area of the lumen to the extent that the monitoring of blood pressure through the lumen is adversely affected. To address this problem, in the case of multiple sensors, this invention provides for positioning the sensors at different longitudinal locations along the distal portion of the transmission means. In the specific case of utilizing an optical fiber for each sensor, the optical fibers terminate distally at staggered locations. Consequently, not all of the sensors are located in the tapered zone, and a larger open area of the tapered zone remains for pressure sensing.

The invention, together with additional features and advantages thereof, may best be understood by reference to the following description taken in connection with the accompanying illustrative drawing.

BRIEF DESCRIPTION OF THE DRAWING

FIG. 1 is a schematic view of an assembly for the in vivo measurement of blood parameters of interest.

FIG. 2 is a perspective view of one form of valve usable in the assembly of FIG. 1.

FIG. 3 is an axial sectional view through the valve with the compliant element being in communication with the conduit leading to the lumen of the catheter.

FIG. 4 is an elevational view partially in section and similar to FIG. 3 with the compliant element being out of communication with the conduit.

FIG. 5 is an enlarged fragmentary sectional view of the distal region of one form of probe and catheter usable in the assembly of FIG. 1.

FIG. 6 is an enlarged sectional view taken generally along line 6—6 of FIG. 5.

FIG. 8 is a sectional view similar to FIG. 5 showing an alternate construction of the distal region of the probe.

FIG. 9 is a schematic view similar to FIG. 1 showing another assembly for the in vivo measurement of blood parameters of interest.

DESCRIPTION OF THE PREFERRED EMBODIMENT

Figure 7:
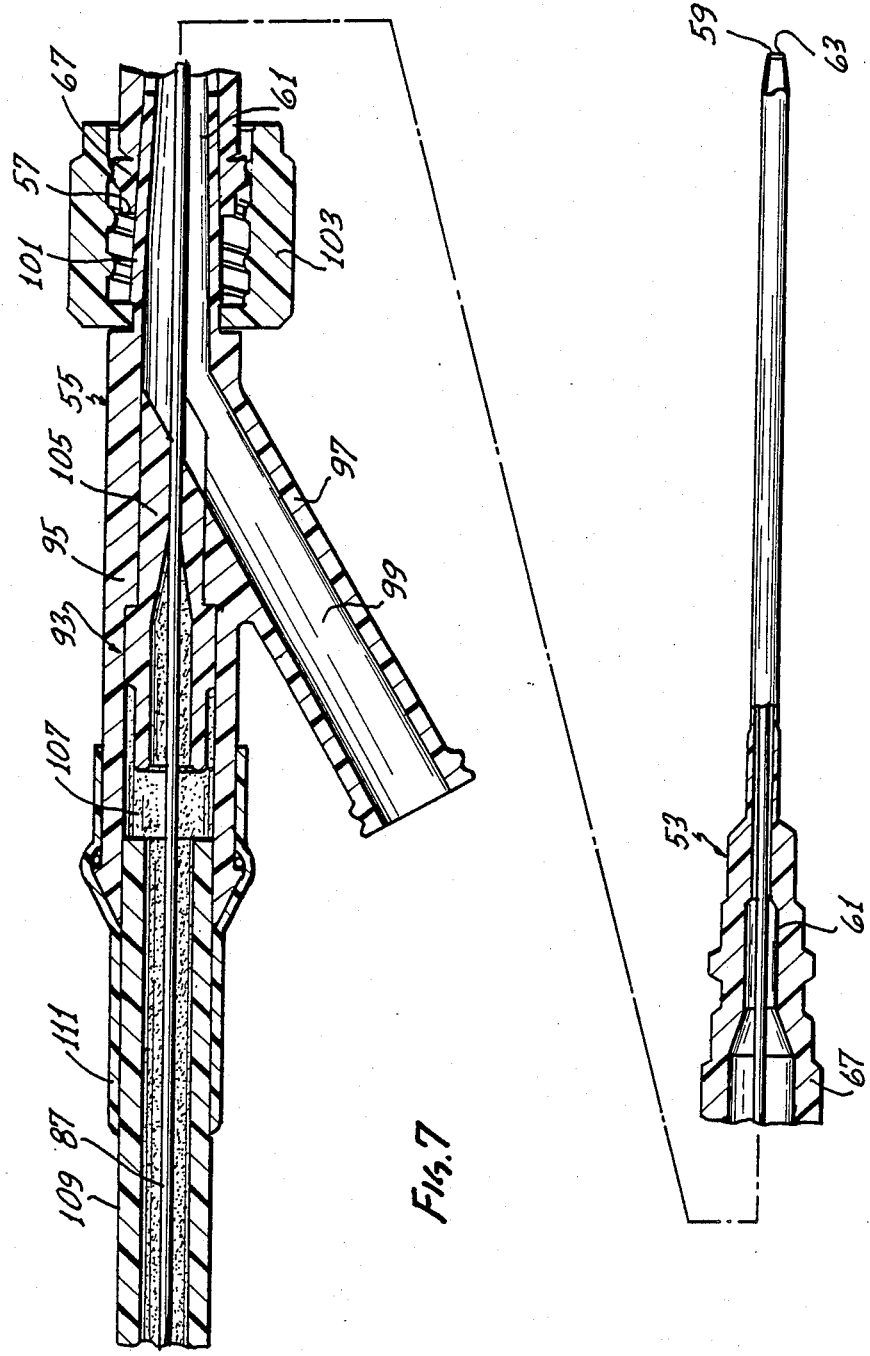
FIG. 7 is a longitudinal sectional view through the probe-catheter assembly.

FIG. 1 shows an assembly 11 for the in vivo measurement of various blood parameters, and particularly the pH value and the concentrations of oxygen and carbon dioxide. Although the assembly 11 can be of different constructions, in this embodiment it includes a solution introducing system 13 and a probe-catheter assembly 15. The assembly 11 may also include an instrument 17 for providing a readout of the blood parameters of interest.

Generally, the solution introducing system 13 introduces an appropriate anti-clotting solution, such as a heparinized saline solution, through the probe-catheter assembly 15 to the patient to keep the line leading to the patient patent. Although this can be accomplished in different ways, in the embodiment shown schematically in FIG. 1, the system 13 includes a pressurized source 19 of heparinized saline solution, a conduit 21 leading from the source to the probe-catheter assembly 15, a flow restrictor 23 to reduce the rate of flow through the conduit 21 to the desired drop rate, a flush valve 25 in a bypass 27 around the restrictor 23, a stop cock 28, a four-way valve 29, a blood withdrawal site 30 and a pressure transducer 31. All of the components of the system 13 may be conventional, and the system 13 may include other components, if desired. In the illustrated embodiment, solution from the pressurized source 19 flows through the restrictor 23 at a relatively slow rate, such as 5 ml/hour. The solution flows through the valve 29 and the probe-catheter assembly 15 to the patient. If a more rapid flow rate from the source 19 is desired, as for example during priming, the flush valve 25 can be manually opened to provide a relatively high-rate flow path around the restrictor 23 in a conventional manner.

The four-way valve 29 may also be of conventional construction. As shown in FIG. 3, the valve 29 includes a valve body 33 having a passage 35 extending therethrough and forming a portion of the conduit 21, a rotatable valve element 37 in the passage 35 and a handle 39 (FIG. 2) for manually rotating the valve element 37. The valve body 33 has a leg 41, and a closure cap 43 is attached to the leg 41 to define, along with the leg, a chamber 45 in which a compliant element in the form of air is located. The valve element 37 has ports 47 and 49 for communicating with the conduit 21, and a port 51 which can communicate with the chamber 45 as shown in FIG. 3 or which can be sealed and out of communication with the conduit 21 and the chamber 45 as shown in FIG. 4. In this manner, the compliant element can be switched into, or out of, the system 13.

The pressure transducer 31 communicates with the conduit 21 and can measure the pressure therein. Accordingly, with the probe-catheter assembly 15 inserted into the vascular system of a patient, the pressure transducer 31 can provide blood pressure readings. By rotating the valve element 37 to the position of FIG. 4, the compliance of the air within the chamber 45 cannot affect the blood pressure readings provided by the transducer 31. The blood withdrawal site 30 is used for taking blood samples from the patient through the probe-catheter assembly 15. Preferably for this kind of compliant element, the stop cock 28 is located between the valve 29 and the site 30 so that, by closing the stop cock 28, the air in the chamber 45 cannot be withdrawn during a blood withdrawal procedure.

The probe-catheter assembly 15 includes a catheter 53 and a probe 55 (FIG. 7). The catheter 53 may be a conventional arterial catheter. As such, the catheter 53 may include a proximal end 57, a distal end 59, a lumen 61 extending axially, completely through the catheter and opening at a distal opening 63 at the distal end. The catheter 53 has a standard lead-in taper, i.e., a tapered zone 65, which extends from a reference plane 66 along the outer periphery of the catheter 53 to the distal end 59. The diameter of the lumen 61 also decreases distally throughout the tapered zone 65 as shown in FIG. 5. The tapered zone 65 may extend about 0.090 inch proximally of the distal end 59. The catheter 53 has an externally threaded coupling 67 at its proximal end.

The probe 55 may be of various different constructions, and in the embodiment illustrated, includes an oxygen sensor 69, a carbon dioxide sensor 71 and a pH sensor 73, with each of the sensors affixed to the distal ends of single optical fibers 75, 77, and 79, respectively, (FIG. 6). In this embodiment, the sensors 69, 71 and 73 are fluorescent optical sensors, and they respond to the concentration of oxygen, the concentration of carbon dioxide and the pH value, respectively, to provide continuous optical signals indicative of the condition sensed. The optical fibers 75, 77 and 79 serve as transmission means for transmitting the signals from the associated sensors proximally. The probe 55 is of very small cross-sectional area so that it fits within the lumen 61 with an ample radial clearance 81 as shown in FIG. 5.

The particular design of the probe 55 forms no part of this invention because this invention is applicable to probes of various different constructions. Briefly, however, the sensors 69, 71 and 73 are attached to the distal ends of the associated optical fibers 75, 77 and 79 in any suitable manner, and each of the sensors and the associated fiber is separately encased in an inner overcoat 83 which, among other things, may assist in retaining the sensor on the end of the associated fiber. The overcoat 83 is, of course, permeable to the relevant blood parameters so that such parameter, or one related to it, can be sensed by the sensors. An outer overcoat 85 covers the inner overcoats 83 and a length of the fibers just proximally of the overcoats 83. Proximally of the overcoat 85, the optical fibers 75, 77 and 79 and a temperature-sensitive element, such as a thermocouple 86 (FIG. 6), are suitably encased within an appropriate sheath 87.

The probe 55 includes a "Y" fitting 93 at its proximal end as shown in FIG. 7. The optical fibers 75, 77 and 79 extend within the sheath 87 completely through one leg 95 of the "Y" fitting 93 to the instrument 17 as shown in FIG. 1. Another leg 97 of the fitting 93 has a passage 99 which communicates with the lumen 61, and more particularly, with the clearance 81 around the probe 55. The leg 97 is coupled to the conduit 21 of the system 13 as shown in FIG. 1. A third leg 101 of the "Y" fitting 93 carries a rotatable internally threaded coupling 103 for attaching the "Y" fitting of the probe 55 to the proximal end of the catheter 53 outside the cardiovascular system of the patient.

Although the details of the fitting 93 form no part of this invention, the sheath 87 may be guided in the leg 95 by a sleeve 105 and retained in position by potting 107. The sheath 87 extends within a flexible tube 109 suitably attached to the leg 95, and shrink tubing 111 is provided over the adjacent end portions of the fitting and the tube for strain relief.

With the proximal end of the catheter 53 coupled to the probe 55 by the coupling 103, the probe 55 is within the lumen 61, and the sensors 69, 71 and 73 are within the lumen adjacent the distal opening 63 as shown in FIG. 5. Accordingly, with the catheter within the cardiovascular system of the patient, such as in a radial artery, the catheter 53 keeps the sensors from contacting the wall of the artery to thereby reduce or eliminate the wall effect and the clot effect on the signals provided by the sensors.

In use of the assembly 11, the catheter 53 is first inserted into the radial artery using conventional techniques. Next, the probe 55 is inserted into the lumen 61 and attached to the proximal end of the catheter 53 with the coupling 103. This properly positions the sensors 69, 71 and 73 within the lumen 61 to within 0.125 inch of the distal end 59. In priming the solution introducing system 13 prior to insertion of the catheter into the artery, a small quantity of air is trapped in the chamber 45. This can be accomplished, for example, with the valve element 37 in the position of FIG. 4, by filling the conduit 21 with solution from the source 19 with the closure cap 43 removed from the valve 29, and without allowing the solution to flow into the leg 41. The closure cap 43 is then affixed to the leg 41 to trap the air in the chamber 45, and then the rotatable valve element 37 is turned to the position shown in FIG. 3. The conduit 21 can then be connected to the probe 55.

When in use, the solution from the source 19 completely fills the lumen 61 around the probe 55. The solution is provided under a pressure such that there is a slow flow of solution from the lumen 61 into the patient's artery. This introduction of the solution through the lumen and into the artery results in an interface 113 adjacent the distal opening 63 which has some axial length and which includes both blood and the solution from the source 19. The interface 113 is a partition between essentially all blood distally of the interface and essentially all anti-clotting solution proximally of the interface. The interface washes axially back and forth in a tidal action as a result of the rising and falling of the patient's blood pressure with each heartbeat. If the solution introducing system 13 were perfectly rigid, it would not be possible for the blood to force the solution proximally within the lumen 61 because the solution is essentially incompressible. However, the conduit 21 is typically in the form of flexible plastic tubing, which has some elasticity or compliance to allow some of this tidal action to occur. In addition, the illustrated embodiment of the invention provides a compliant element in the form of air within the chamber 45 which adds additional elasticity or compliance to the system 13. Consequently, the interface can flow back and forth to bathe the sensors 69, 71 and 73 in blood.

With this embodiment of the invention, the back and forth travel of the interface 113 is a function of the magnitude of the patient's blood pressure, the compliance of the solution-introducing system 13 and the delivery pressure of the anti-clotting solution. However, assuming that there is some net flow of the anti-clotting solution out of the distal opening 63, it would be necessary for at least the distal region of the interface 113 to travel distally as far as the distal opening, unless it is possible for some of the solution to migrate through the blood and through the distal opening. Because the flow rate of anti-clotting solution into the bloodstream is extremely low, the precise manner in which the solution enters the patient's bloodstream and the exact extent of travel of the interface 113 is not known. However, utilizing the tidal action of the interface, it is possible to bathe the sensors 69, 71 and 73 in blood sufficiently so that accurate readings are obtained, and it is believed that the sensors are in essentially all blood for a majority of the time.

FIG. 8 shows another embodiment of this invention which is identical to the embodiment of FIGS. 1–7 in all respects not shown or described herein. Portions of the embodiment of FIG. 8 corresponding to portions of the embodiment of FIGS. 1–7 are designated by corresponding reference numerals followed by the letter "a."

The primary differences between the embodiment of FIG. 8 and FIGS. 1–7 is that the sensors 69a, 71a, and 73a are at different longitudinal positions within the lumen 61a, the sensors 71a and 73a project farther from the overcoat 85a, and there are a plurality of radial apertures 121 in the catheter 53a leading from the lumen 61a adjacent the distal opening 63a of the catheter. In this embodiment, each of the three sensors terminates at a different axial position within the lumen 61a, and with this construction, the total cross-sectional area of the probe 55a reduces in step-wise fashion from the distal end of the sensor 71a proximally. Consequently, not all of the sensors are in the tapered zone 65a, and a larger cross-sectional area of the tapered zone remains open for pressure sensing via the pressure transducer 31 shown in FIG. 1.

In the construction of FIG. 8, preferably the carbon dioxide sensor 71a is the most distal sensor, and the oxygen sensor 69a is the most proximal. The reason for this is that carbon dioxide is the most sensitive to being even partially out of the blood, and the oxygen sensor can provide acceptable oxygen readings even in a fifty-fifty mixture of the blood and the anti-clotting solution. The sensitivity of the pH sensor 73a is intermediate the sensitivity of the carbon dioxide sensor 71a and the oxygen sensor 73a and so is preferably located intermediate these sensors.

The radial apertures 121 are preferably located proximally of the sensor 73a for the purpose of allowing blood and solution from the lumen 61a to flow out of the apertures. One or more of these apertures may be provided, and in the embodiment of FIG. 8, two of the apertures are shown. Of course, the apertures 121 may be distributed in axially spaced relationship, as well as circumferentially spaced relationship, along the catheter 53a. The apertures 121 may also be used in the embodiment of FIGS. 1–7, if desired.

FIG. 9 shows another embodiment of this invention which is identical to the embodiment of FIGS. 1–7 in all respects not shown or described herein. Portions of the embodiment of FIG. 9 corresponding to portions of the embodiment of FIGS. 1–7 are designated by corresponding reference numerals followed by the letter "b."

The only difference between the embodiment of FIG. 9 and FIGS. 1–7 is that the valve 29 has been replaced with a volume oscillator 131. Although the volume oscillator 131 can take different forms, including that of a conventional syringe, in this embodiment, it is illustrated schematically as including a cylinder 133 in communication with the conduit 21, a piston 135 slidable in the cylinder and a motor 137 for reciprocating the piston 135 through an appropriate reciprocating drive (not shown), such as a cam shaft. When the piston 135 is moved upwardly as viewed in FIG. 9, a chamber 139 below the piston is enlarged to expand the volume of the introducing system 13b. Conversely, when the piston 135 moves downwardly, the volume of the chamber 139 is decreased to thereby contract the volume of the introducing system. Of course, expansion of the introducing system 13b pulls the interface 113 (FIG. 5) proximally. Contraction of the introducing system moves the interface distally, with the amount of such movement being a function of the degree to which the volume oscillator 131 expands and contracts the volume of the introducing system.

The motor 137 can be operated continuously, intermittently or upon demand to create the tidal action. There is no net or average flow of fluid in either direction as a result of reciprocation of the piston 135. Of course, the volume oscillator 131 can also be used with the embodiment of FIG. 8.

Although exemplary embodiments of the invention have been shown or described, many changes, modifications and substitutions may be made by one having ordinary skill in the art without necessarily departing from the spirit and scope of this invention.

I claim:

1. A probe for sensing at least one parameter in blood comprising:
   first and second optical sensors for sensing at least one parameter in blood selected from the group consisting of blood gases, pH, electrolytes, glucose, and temperature and for providing a signal in response thereto; and
   elongated transmission means for transmitting the signals from the first and second sensors proximally;
   said first and second sensors being carried by a distal portion of the transmission means with the first and second sensors being at different longitudinal positions along the distal portion of the transmission means; and
   said transmission means and said first and second sensors being sized to be received in the cardiovascular system of a patient.

2. A probe as defined in claim 1 wherein said transmission means includes means for transmitting light.

3. A probe as defined in claim 1 wherein said transmission means includes means for transmitting light and said first sensor is a fluorescent sensor.

4. A probe as defined in claim 1 wherein said first and second sensors sense first and second different parameters in blood, respectively, and said first and second parameters are different blood gases.

5. A probe as defined in claim 1 wherein said first and second sensors sense first and second different parameters in blood, respectively, and said first and second parameters are a blood gas and pH, respectively.

6. A probe as defined in claim 1 wherein said transmission means includes first and second elongated optical fibers, each of said first and second optical fibers has a distal end, said first and second sensors are carried by the first and second optical fibers, respectively, adjacent the distal ends thereof, and said first optical fiber extends distally beyond the second optical fiber.

7. A probe as defined in claim 6 wherein said first and second sensors sense first and second different parameters in blood, respectively, and said first and second parameters are different blood gases.

8. A probe as defined in claim 6 wherein said first and second sensors sense first and second different parameters in blood, respectively, and said first and second parameters are a blood gas and pH, respectively.

9. A probe as defined in claim 6 including a third optical sensor for sensing a parameter in blood, said transmission means includes a third elongated optical fiber having a distal end, said third optical sensor being carried by the third optical fiber adjacent the distal end thereof, and said second optical fiber extends distally beyond the third optical fiber.

10. A probe as defined in claim 1 wherein said first and second sensors sense oxygen and carbon dioxide and the first sensor is located proximally of the second sensor.

11. A probe for sensing at least one parameter in blood comprising:
    first and second sensors for sensing at least one parameter in blood selected from the group consisting of blood gases, ph, electrolytes, glucose, and temperature and for providing a signal in response thereto; and
    first and second elongated optical fibers, each of said first and second optical fibers having a distal end portion which terminates in a distal end, said first and second sensors being optical sensors and being carried by the first and second optical fibers, respectively, adjacent the distal ends thereof;
    said first optical fiber extending distally along the distal end portion of the second optical fiber and distally beyond the distal end of the second optical fiber; and
    said first and second optical fibers and said first and second sensors being sized to be received in the cardiovascular system of a patient.

12. A probe as defined in claim 11 wherein said first sensor is a fluorescent sensor.

13. A probe as defined in claim 11 wherein said first and second sensors sense first and second different parameters in blood, respectively, and said first and second parameters are different blood gases.

14. A probe as defined in claim 11 wherein said first and second sensors first and second different parameters in blood, respectively, and said first and second parameters are a blood gas and pH, respectively.

15. A probe as defined in claim 11 including a third optical sensor for sensing a parameter in blood and a third elongated optical fiber having a distal end portion which terminates in a distal end, said third optical sensor being carried by the third optical fiber adjacent the distal end thereof, and said second optical fiber extends distally along the distal end portion of the third optical fiber and distally beyond the distal end of the third optical fiber.

16. An assembly for sensing at least one parameter in blood comprising:
    a catheter having a lumen extending therethrough and being sized to be received in the cardiovascular system of a patient; and
    a probe including first and second optical sensors for sensing at least one parameter in blood selected from the group consisting of blood gases, pH, electrolytes, glucose, and temperature and for providing a signal in response thereto and elongated transmission means for transmitting the signals from the first and second optical sensors proximally, said first and second optical sensors being carried by a distal portion of the transmission means with the first and second optical sensors being at different longitudinal positions along the distal portion of the transmission means, and said elongated transmission means extending into said lumen and said first and second optical sensors being within said lumen.

17. An assembly as defined in claim 16 wherein the lumen has a distal opening and the sensors are adjacent the distal opening.

18. An assembly as defined in claim 17 wherein the lumen is of reducing cross section toward the distal opening in a tapered zone adjacent the distal opening and the first and second sensors are in the tapered zone.

19. A probe for sensing parameters in blood comprising:
    first and second sensors for sensing first and second different parameters in blood, respectively, said parameters being selected from the group consisting of blood gases, pH, electrolytes, and temperature and for providing a signal in response thereto; and
    elongated transmission means for transmitting the signals from the first and second sensors proximally;
    said first and second sensors being carried by a distal portion of the transmission means with the first and second sensors being at different longitudinal positions along the distal portion of the transmission means; and
    said transmission means and said first and second sensors being sized to be received in the cardiovascular system of a patient.

20. A probe as defined in claim 19 wherein said first and second parameters are different blood gases.

21. A probe as defined in claim 19 wherein said first and second parameters are a blood gas and pH, respectively.

* * * * *

UNITED STATES PATENT AND TRADEMARK OFFICE
CERTIFICATE OF CORRECTION

PATENT NO. : 4,928,694

DATED : May 29, 1990

INVENTOR(S) : Thomas P. Maxwell

It is certified that error appears in the above-identified patent and that said Letters Patent is hereby corrected as shown below:

Col. 10, line 39, delete "ph" and insert therefor --pH--.

Col. 10, line 62, after "sensors" insert --sense--.

Signed and Sealed this

Eighth Day of October, 1991

*Attest:*

HARRY F. MANBECK, JR.

*Attesting Officer*   *Commissioner of Patents and Trademarks*

UNITED STATES PATENT AND TRADEMARK OFFICE
CERTIFICATE OF CORRECTION

PATENT NO. : B1 4,928,694
DATED : June 6, 1995
INVENTOR(S) : Thomas P. Maxwell

It is certified that error appears in the above-indentified patent and that said Letters Patent is hereby corrected as shown below:

Column 1, line 41, delete "poriton" and insert therefor --portion--.

Column 1, line 43, delete "logitudinal" and insert therefor --longitudinal--.

Column 2, line 14, delete "logitudinal" and insert therefor --longitudinal--.

Column 2, line 15, delete "sending" and insert therefor --sensing--.

Column 2, line 45, delete "wheren" and insert therefor --wherein--.

Column 3, line 45, delete "respectivley" and insert therefor --respectively--.

Column 4, line 14, delete "assmebly" and insert therefor --assembly--.

Column 4, line 21, delete "form" and insert therefor --from--.

Column 4, line 22, delete "electroytes" and insert therefor --electrolytes--.

Column 4, line 31, delete "poriton" and insert therefor --portion--.

UNITED STATES PATENT AND TRADEMARK OFFICE
CERTIFICATE OF CORRECTION

PATENT NO. : B1 4,928,694

DATED : June 6, 1995

INVENTOR(S) : Thomas P. Maxwell

It is certified that error appears in the above-indentified patent and that said Letters Patent is hereby corrected as shown below:

Column 4, line 58, delete "wherien" and insert therefor --wherein--.

Signed and Sealed this

Seventeenth Day of October, 1995

Attest:

BRUCE LEHMAN

Attesting Officer          Commissioner of Patents and Trademarks

REEXAMINATION CERTIFICATE (2593rd)
United States Patent [19]
Maxwell

[11] B1 4,928,694
[45] Certificate Issued  Jun. 6, 1995

[54] INTRAVASCULAR BLOOD PARAMETER MEASUREMENT SYSTEM

[75] Inventor: Thomas P. Maxwell, Santa Ana, Calif.

[73] Assignee: Minnesota Mining and Manufacturing Company, Saint Paul, Minn.

Reexamination Request:
No. 90/003,443, May 25, 1994

Reexamination Certificate for:
Patent No.: 4,928,694
Issued: May 29, 1990
Appl. No.: 328,041
Filed: Mar. 23, 1989

Certificate of Correction issued Oct. 8, 1991

Related U.S. Application Data

[62] Division of Ser. No. 8,937, Jan. 30, 1987, Pat. No. 4,830,013.

[51] Int. Cl.⁶ .............................................. A61B 5/00
[52] U.S. Cl. ...................................... 128/637; 128/634
[58] Field of Search ................. 128/632, 634.5, 637, 128/673, 692

[56] References Cited

U.S. PATENT DOCUMENTS

| Number | Date | Name |
|---|---|---|
| Re. 31,879 | 5/1985 | Lubbers et al. |
| 2,629,399 | 2/1953 | Kulick |
| 3,433,935 | 3/1969 | Sherman |
| 3,461,856 | 8/1969 | Polanyi |
| 3,498,286 | 3/1970 | Polanyi et al. |
| 3,512,517 | 5/1970 | Kadish et al. |
| 3,529,591 | 9/1970 | Schuette |
| 3,604,263 | 9/1971 | Auphan et al. |
| 3,612,866 | 10/1971 | Stevens |
| 3,616,409 | 10/1971 | Tosteson |
| 3,658,053 | 4/1972 | Fergusson et al. |
| 3,674,013 | 7/1972 | Polanyi |
| 3,807,390 | 4/1974 | Ostrowski et al. |
| 3,814,081 | 6/1974 | Mori |
| 3,841,308 | 10/1974 | Tate |
| 3,866,599 | 2/1975 | Johnson |
| 3,878,830 | 4/1975 | Bicher |
| 3,893,448 | 7/1975 | Brantigan |
| 3,983,864 | 10/1976 | Sielaff et al. |
| 4,050,450 | 9/1977 | Polanyi et al. |
| 4,073,297 | 2/1978 | Kopp |
| 4,120,292 | 10/1978 | LeBlanc, Jr. et al. |
| 4,187,856 | 2/1980 | Hall et al. |
| 4,200,110 | 4/1980 | Peterson et al. |
| 4,201,222 | 5/1980 | Haase |
| 4,210,029 | 7/1980 | Porter |
| 4,265,249 | 5/1981 | Schindler et al. |
| 4,274,417 | 6/1981 | Delpy |
| 4,295,470 | 10/1981 | Shaw et al. |
| 4,311,137 | 1/1982 | Gerard |
| 4,321,057 | 3/1982 | Buckles |
| 4,322,164 | 3/1982 | Shaw et al. |
| 4,340,615 | 7/1982 | Goodwin et al. |
| 4,397,314 | 8/1983 | Vaguine |
| 4,398,542 | 8/1983 | Cunningham et al. |
| 4,399,099 | 8/1983 | Buckles |
| 4,407,290 | 10/1983 | Wilbur |

(List continued on next page.)

FOREIGN PATENT DOCUMENTS

| 2215984 | 10/1972 | Germany |
| 106086 | 8/1974 | Germany |
| 3038883 | 7/1982 | Germany |
| 1593270 | 7/1981 | United Kingdom |
| 2108675 | 5/1983 | United Kingdom |

*Primary Examiner*—Angela D. Sykes

[57] ABSTRACT

A parameter of blood is sensed in vivo with a system which includes a catheter and a probe. The catheter has a lumen extending therethrough, a proximal end, a distal end and a distal opening at the distal end. The probe includes one or more sensors at its distal end. A saline solution is introduced into the lumen so that there is an interface adjacent the distal opening of the catheter between the blood and saline solution. The probe is received within the catheter and affixed thereto. The interface is moved back and forth in the lumen to expose the sensors to blood so that they can sense the blood parameters of interest.

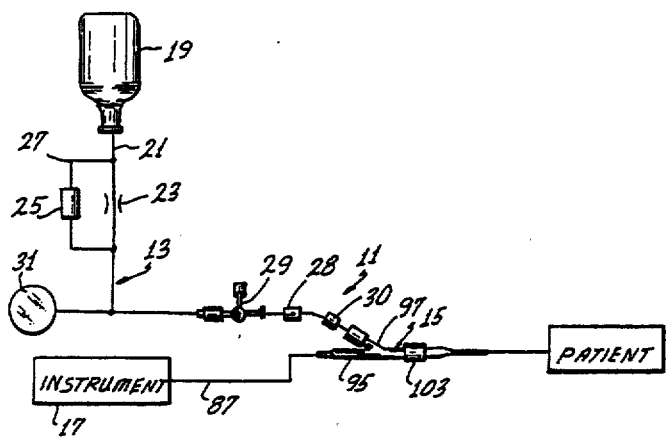

U.S. PATENT DOCUMENTS

| | | |
|---|---|---|
| 4,444,198 | 4/1984 | Petre . |
| 4,448,547 | 5/1984 | Wickersheim . |
| 4,471,765 | 9/1984 | Strauss et al. . |
| 4,476,870 | 10/1984 | Peterson et al. . |
| 4,476,877 | 10/1984 | Barker . |
| 4,478,222 | 10/1984 | Koning et al. . |
| 4,502,488 | 3/1985 | Degironimo et al. . |
| 4,508,123 | 4/1985 | Wyatt et al. . |
| 4,535,786 | 8/1985 | Kater . |
| 4,543,961 | 10/1985 | Brown . |
| 4,557,900 | 12/1985 | Heitzmann . |
| 4,573,968 | 3/1986 | Parker . |
| 4,585,007 | 4/1986 | Uchigaki et al. . |
| 4,601,706 | 7/1986 | Aillón . |
| 4,608,996 | 9/1986 | Brown . |
| 4,622,974 | 11/1986 | Coleman et al. . |
| 4,640,820 | 2/1987 | Cooper . |
| 4,651,741 | 3/1987 | Passafaro . |
| 4,682,895 | 7/1987 | Costello . |
| 4,684,245 | 8/1987 | Goldring . |
| 4,703,756 | 11/1987 | Gough et al. . |
| 4,706,677 | 11/1987 | Goorsky et al. . |
| 4,718,423 | 1/1988 | Willis et al. . |
| 4,727,730 | 3/1988 | Boiarski et al. . |
| 4,735,619 | 4/1988 | Sperry et al. . |
| 4,736,748 | 4/1988 | Nakamura et al. . |
| 4,749,254 | 6/1988 | Seaver . |
| 4,752,115 | 6/1988 | Murray, Jr. et al. . |
| 4,774,955 | 10/1988 | Jones . |
| 4,810,655 | 3/1989 | Khalil et al. . |
| 4,841,974 | 6/1989 | Gumbrecht et al. . |
| 4,854,321 | 8/1989 | Boiarski . |

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentabilty of claims 17 and 18 is confirmed.

Claims 2, 7-8, 10 and 19-21 are cancelled.

Claims 1, 3-6, 9 and 11-16 are determined to be patentable as amended.

New claims 22-40 are added and determined to be patentable.

1. A probe for sensing at least one parameter in blood comprising:
    (a) first and second optical sensors for sensing at least one parameter in blood selected from the group consisting of blood gases, pH, electrolytes, glucose, and temperature, and for providing a signal in repsonse thereto; [and]
    (b) *first and second elongated optical fibers* [elongated tranmission means] for transmitting the signals from the first and second sensors proximally, *each of the first and second optical fibers having a free distal end with a distal end portion adjacent thereto;*
    (c) [said] *the* first and second sensors being carried by [a] *the* distal end portions of the *first and second optical fibers, respectively, and the distal end portion of the first optical fiber extends distally beyond* the distal end poritón of the second optical fiber [transmission means] with the first and second sensors being at different logitudinal positions [along the distal portion of the transmission means]; and
    (d) *the first and second elongated optical fibers* [said transmission means] and [said] *the* first and second sensors being sized to be received in the cardiovascular system of a patient.

3. A probe as defined in claim 1 wherein [said transmission means includes means for transmitting light and said] *the* first sensor is a fluorescent sensor.

4. A probe as defined in claim 1 wherein *the* [said] first and second sensors sense first and second different parameters in blood, respectively, and [said] *the* first and second different parameters are different blood gases.

5. A probe as defined in claim 1 wherein [said] *the* first and second sensors sense first and second different parameters in blood, respectively, and [said] *the* first and second different parameters are a blood gas and pH[, respectively].

6. A probe as defined in claim 1 wherein [said transmission means includes first and second elongated optical fibers, each of said first and second optical fibers has a distal end, said] *at least one of the* first and second sensors [are] *is* carried by [the first and second] *its respective* optical [fibers, respectively,] *fiber* adjacent the distal [ends] *end* thereof[, and said first optical fiber extends distally beyond the second optical fiber].

9. A probe as defined in claim 1 [6] *further* including a third optical sensor for sensing a parameter in blood, [said transmission means includes] *and* a third elongated optical fiber having a distal end *portion which terminates in a distal end*, [said] *the* third optical sensor being carried by the *distal end portion of the* third optical fiber [adjacent the distal end thereof], and [said] *the distal end portion of the* second optical fiber extends distally beyond the *distal end portion of the* third optical fiber *with the first, second, and third optical sensors each being at a different logitudinal position.*

11. A probe for sending [at least one] [parameter] parameters in blood comprising:
    (a) first and second *optical* sensors for sensing *first and second different* [at least one] [parameter] *parameters* in blood, *respectively, the parameters being selected from the group consisting of blood gases, pH, electrolytes, glucose, and temperature,* and for providing a signal in response thereto; [and]
    (b) first and second elongated optical fibers *for transmitting the signals from the first and second sensors proximally,* each of [said] *the* first and second optical fibers having a *free* distal end *with a distal end* portion *adjacent thereto;* [which terminates in a distal end,]
    (c) [said] *the* first and second sensors being [optical sensors and being] carried by the first and second optical fibers, respectively, adjacent the distal ends thereof, *and the distal end portion of the* [said] first optical fiber [extending] extends [distally along the distal end portion of the second optical fiber and] distally beyond the distal end portion of the second optical fiber *with the first and second sensors terminating at different axial positions*; and
    (d) [said] *the* first and second *elongated* optical fibers and [said] *the* first and second sensors being sized to be received in the cardiovascular system of a patient.

12. A probe as defined in claim 11 wherein [said] *the* first sensor is a fluorescent sensor.

13. A probe as defined in claim 11 wheren [said first and second sensors sense first and second different parameters in blood, respectively, and said] *the* first and second *different* parameters are different blood gases.

14. A probe as defined in claim 11 wherein [said first and second sensors sense first and second different parameters in blood, respectively, and said] *the* first and second *different* parameters are a blood gas and pH[, respectively].

15. A probe as defined in claim 11 *further* including a third optical sensor for sensing a *third different* parameter in blood, and a third elongated optical fiber having a distal end portion which terminates in a distal end, [said] *the* third optical sensor being carried by the third optical fiber adjacent the distal end thereof, and [said] *the distal end portion of the* second optical fiber extends [distally along the distal end portion of the third optical fiber and] distally beyond the distal end *portion* of the third optical fiber *with the first, second, and third sensors each terminating at a different axial position.*

16. An assembly for sensing at least one parameter in blood comprising:

(a) a catheter having a lumen extending therethrough and being sized to be received in the cardiovascular system of a patient; and (b) a probe including (i) first and second optical sensors for sensing at least one parameter in blood selected from the group consisting of blood gases, pH, electrolytes, glucose, and temperature, and for providing a signal in response thereto; [and] (ii) first and second elongated [transmission means] optical fibers for transmitting the signals from the first and second optical sensors proximally, *each of the first and second optical fibers having a free distal end with a distal end portion adjacent thereto;* (iii) [said] *the* first and second optical sensors being carried by [a] *the* distal end portion of the *first and second optical fibers, respectively,* [transmission means with] *and* the *distal end portion of the first optical fiber extends distally beyond the distal end portion of the second optical fiber with the* first and second optical [fibers] *sensors* being at different longitudinal positions [along the distal portion of the transmission means]; and (iv) [said] *the first and second* elongated [transmission means] *optical fibers* extending into [said] *the* lumen and [said] *the* first and second optical sensors being within [said] *the* lumen.

22. A probe as defined in claim 4 wherein the first and second different parameters are oxygen and carbon dioxide.

23. A probe as defined in claim 9 wherein the first, second, and third sensors sense first, second, and third different parameters in blood, respectively, and the first, second, third different parameters are carbon dioxide, pH, and oxygen.

24. A probe as defined in claim 9 wherein each of the first, second, and third sensors is carried by its respective optical fiber adjacent the distal end thereof.

25. A probe as defined in claim 15 wherein the first, second, and third different parameters are carbon dioxide, pH, and oxygen.

26. An assembly as defined in claim 16 wherein the first sensor is a fluorescent sensor.

27. An assembly as defined in claim 16 wherein the first and second sensors sense first and second different parameters in blood, respectivley, and the first and second different parameters are different blood gases.

28. An assembly as defined in claim 27 wherein the first and second different parameters are oxygen and carbon dioxide.

29. An assembly as defined in claim 16 wherein the first and second sensors sense first and second different parameters in blood, respectively, and the first and second different parameters are a blood gas and pH.

30. An assembly as defined in claim 16 wherein at least one of the first and second sensors is carried by its respective optical fiber adjacent the distal end thereof.

31. An assembly as defined in claim 16 wherein the probe further includes a third optical sensor for sensing a parameter in blood, and a third elongated optical fiber having a distal end portion which terminates in a distal end, the third optical sensor being carried by the distal end portion of the third optical fiber, and the distal end portion of the second optical fiber extends distally beyond the distal end portion of the third optical fiber with the first, second, and third optical sensors each being at a different longitudinal position.

32. An assembly as defined in claim 31 wherein the first, second, and third sensors sense first, second, and third different parameters in blood, respectively, and the first, second, third different parameters are carbon dioxide, pH, and oxygen.

33. An assembly as defined in claim 31 wherein each of the first, second, and third sensors is carried by its respective optical fiber adjacent the distal end thereof.

34. *An assmebly for sensing parameters in blood comprising:*

(a) *a catheter having a lumen extending therethrough and being sized to be received in the cardiovascular system of a patient; and*

(b) *a probe including (i) first and second optical sensors for sensing first and second different parameters in blood, respectvely, the parameters being selected form the group consisting of blood gases, pH, electroytes, glucose, and temperature, and for providing a signal in response thereto; (ii) first and second elongated optical fibers for transmitting the signals from the first and second sensors proximally, each of the first and second optical fibers having a free distal end with a distal end portion adjacent thereto; (iii) the first and second sensors being carried by the first and second optical fibers, respectively, adjacent the distal ends thereof, and the distal end poriton of the first optical fiber extends distally beyond the distal end portion of the second optical fiber with the first and second sensor terminating at different axial positions; and (iv) the first and second elongated optical fibers extending into the lumen, and the first and second optical sensors being within the lumen.*

35. *An asssembly as defined in claim 34 wherein the first and second different parameters are different blood gases.*

36. *An assembly as defined in claim 34 wherein the first and second different parameters are a blood gas and pH.*

37. *An assembly as defined in claim 34 wherein the lumen has a distal opening and the sensors are adjacent the distal opening.*

38. *An assembly as defined in claim 37 wherein the lumen is of reducing cross section toward the distal opening in a tapered zone adjacent the distal opening and the first and second sensors are in the tapered zone.*

39. *An assembly as defined in claim 34 further including a third optical sensor for sensing a third different parameter in blood, and a third elongated optical fiber having a distal end portion which terminates in a distal end, the third optical sensor being carried by the third optical fiber adjacent the distal end thereof, and the distal end portion of the second optical fiber extends distally beyond the distal end portion of the third optical fiber.*

40. *An assembly as defined in claim 39 wherien said first, second, and third different parameters are carbon dioxide, pH, and oxygen.*

* * * * *